(12) United States Patent
Way et al.

(10) Patent No.: US 8,835,584 B2
(45) Date of Patent: Sep. 16, 2014

(54) COPOLYMER AND METHOD FOR MANUFACTURING THE SAME

(75) Inventors: Tun-Fun Way, Hsinchu (TW); Yu-Ting Chen, Tianzhong Township, Changhua County (TW); Jiun-Jy Chen, Toufen Township, Miaoli County (TW); Kelly Teng, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 36 days.

(21) Appl. No.: 13/619,246

(22) Filed: Sep. 14, 2012

(65) Prior Publication Data

US 2013/0172490 A1 Jul. 4, 2013

(30) Foreign Application Priority Data

Dec. 30, 2011 (TW) .............................. 100149766 A (51) Int. Cl.
 C08F 20/06 (2006.01)
 C08F 20/56 (2006.01)
 C08F 20/58 (2006.01)
 C08F 228/02 (2006.01)

(52) U.S. Cl.
 USPC ........... 526/312; 526/89; 526/218.1; 526/304

(58) Field of Classification Search
 USPC ......... 526/89, 218.1, 219, 286, 304, 310, 312
 See application file for complete search history.

(56) References Cited

U.S. PATENT DOCUMENTS

| | | | |
|---|---|---|---|
| 3,992,333 A | 11/1976 | Emmons et al. | |
| 4,391,878 A | 7/1983 | Drach | |
| 5,163,115 A | 11/1992 | Sheu | |
| 5,854,364 A * | 12/1998 | Senninger et al. | ............ 526/192 |
| 6,689,378 B1 | 2/2004 | Sun | |
| 7,173,085 B2 | 2/2007 | Eknoian | |
| 2009/0186158 A1 | 7/2009 | Eisenhuth | |
| 2011/0001904 A1 | 1/2011 | Tachikawa et al. | |
| 2011/0133330 A1 | 6/2011 | Bai | |

FOREIGN PATENT DOCUMENTS

| | | |
|---|---|---|
| CN | 101348544 | 1/2009 |
| TW | 200951194 | 12/2009 |

OTHER PUBLICATIONS

Marcela Urzu et al., "Blends Containing Amphiphilic Polymers IV. Poly(N-1-alkylltaconamic Acids) with Poly(2-vinylpyridine) and Poly(4-vinylphenol)", Journal of Applied Polymer Science, 2002, vol. 84, 1245-1250.

Marcela Urzu et al. "Blends Containing Amphiphilic Polymers.V. Compatibilization of N-Alkylitaconamic Acid-co-Styrene Copolymers with Interacting Polymers", Journal of Applied Polymer Science, 2006, vol. 102, 2512-2519.

Anjali Solanki et al., "Effect of structure on thermal behavior of homopolymers and copolymers of itaconimides", J. Macromol. Sci.—Polymer Reviews, 2001, (2001), C41(4), 253-284.

Tao Wan et al., "Saline solution absorbency and structure study of poly(AA-AM) water superabsorbent by inverse microemulsion polymerization", Polymer Bulletin, 2008, 60, 431-440.

B.L. Rivas et al., "Synthesis, Characterization, and Polychelatogenic Properties of Poly (acrylic acid-co-acrylamide)", Journal of Polymer Science: Part A: Polym. Chem., 1997, vol. 35, 2461-2467.

Office Action and Search Report from TW 100149766, mailed Feb. 21, 2014, pp. 1-4.

* cited by examiner

*Primary Examiner* — Irina S Zemel
*Assistant Examiner* — Jeffrey Lenihan
(74) *Attorney, Agent, or Firm* — Muncy, Geissler, Olds & Lowe, P.C.

(57) ABSTRACT

In one embodiment of the disclosure, a copolymer and method for manufacturing the same are provided. The copolymer is copolymerized from a composition including: (a) a first hydrophilic monomer, including itaconamic acid, itaconamic salt, or combinations thereof; and (b) a second hydrophilic monomer, including acrylic acid, acrylic salt, acrylamide, or combinations thereof.

25 Claims, 2 Drawing Sheets

COPOLYMER AND METHOD FOR MANUFACTURING THE SAME

CROSS REFERENCE TO RELATED APPLICATIONS

This application claims priority of Taiwan Patent Application No. 100149766, filed on Dec. 30, 2011, the entirety of which is incorporated by reference herein.

TECHNICAL FIELD

The technical field relates to a copolymer and method for manufacturing the same.

BACKGROUND

Superabsorbent polymers (SAP) have been widely applied in the sanitation, medical, and agriculture industries, and also other various industries. For example, superabsorbent polymers have been used in diapers, sanitary pads, or the like.

Concerns about using superabsorbent polymers are that the absorbent ability decreases severely in saline solution. In general, water absorption rate of a superabsorbent polymer in distilled water (for example, about 250 g/g) is much higher than the water absorption rate of the superabsorbent polymer in normal saline (for example, about 61 g/g.) Moreover, the water absorption rate of the superabsorbent polymer in normal saline may drop drastically under pressure (for example, 35 g/g.) In other words, the water absorption rate of the superabsorbent polymer in a saline environment may be one-seventh of that in the distilled water, such that seven times that the amount of the superabsorbent polymer is required to achieve the same absorption rate. Therefore, sanitary products such as diapers and sanitary pads are thick, and heavy.

SUMMARY

An embodiment of the disclosure provides a copolymer copolymerized from a composition including: (a) a first hydrophilic monomer, including itaconamic acid, itaconamic salt, or combinations thereof; and (b) a second hydrophilic monomer, including acrylic acid, acrylic salt, acrylamide, or combinations thereof.

An embodiment of the disclosure provides a method for manufacturing a copolymer, including copolymerizing a composition using a free radical polymerizing reaction, wherein the composition includes: (a) a first hydrophilic monomer, including itaconamic acid, itaconamic salt, or combinations thereof; and (b) a second hydrophilic monomer, including acrylic acid, acrylic salt, acrylamide, or combinations thereof.

A detailed description is given in the following embodiments with reference to the accompanying drawings.

BRIEF DESCRIPTION OF THE DRAWINGS

The embodiments can be more fully understood by reading the subsequent detailed description and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In various embodiments of the disclosure, a novel copolymer is provided. The copolymer has a high density of a carboxylic group and amino group, and therefore the copolymer can be used as a great chelating agent, water-absorbing agent, sealant, or fire retardant. In addition, when a crosslinker is used during the polymerization process, a superabsorbent polymer having high water absorption ability in both pure water or silane can be formed.

In one embodiment, a method for manufacturing a novel copolymer is provided. The method includes copolymerizing a composition using a free radical polymerizing reaction, wherein the composition includes: (a) a first hydrophilic monomer, including itaconamic acid (IAm), itaconamic salt, or combinations thereof; and (b) a second hydrophilic monomer, including acrylic acid (AA), acrylic salt, acrylamide (Am), or combinations thereof. In one embodiment, the composition contains 1.0 wt % to 60 wt % of the first hydrophilic monomer. In another embodiment, the composition contains 10 wt % to 30 wt % of the first hydrophilic monomer. In still another embodiment, the composition contains 30 wt % to 99 wt % of acrylic acid or acrylic salt of the second hydrophilic monomer. In still another embodiment, the composition contains 45 wt % to 90 wt % of acrylic acid or acrylic salt of the second hydrophilic monomer. In addition, the composition may contain 1.0 wt % to 60 wt % of acrylamide of the second hydrophilic monomer, for example. In another embodiment, the composition contains 10 wt % to 33 wt % of acrylamide of the second hydrophilic monomer. Note that the itaconamic salt and acrylic salt may refer to, for example, lithium salt, sodium salt, potassium salt, magnesium salt, aluminum salt, calcium salt, or combinations thereof. In one embodiment, a weight-average molecular weight of the copolymer is between 11,000 g/mole and 23,000 g/mole. In another embodiment, the composition further includes a crosslinker so that a superabsorbent polymer can be formed. Examples of the crosslinker includes N,N'-methylenebisacrylamide, polyethylene glycol diacrylate, trimethylolpropane ethoxylate triacrylate, pentaerythritol triacrylate, or combinations thereof. The crosslinker may be present in an amount of 0.5 wt % to 5 wt % of the total amount of the first hydrophilic monomer and the second hydrophilic monomer. In another embodiment, the crosslinker may be present in an amount of 0.5 wt % to 3 wt % of the total amount of the first hydrophilic monomer and the second hydrophilic monomer. In still another embodiment, the crosslinker may be present in an amount of 1 wt % of the total amount of the first hydrophilic monomer and the second hydrophilic monomer.

The copolymer described above has a high density of a carboxylic group and amino group, and therefore the copolymer can be used as a good chelating agent, for example, used for purification or waste water treatment. Alternatively, the copolymer may be used as a water-absorbing agent, wherein a water absorption rate of the copolymer may reach 31 g/g to 51 g/g (placed in 0.9 wt % of sodium chloride solution and centrifuged at 1500 rpm.) In addition, the copolymer may also be used as a sealant, expandable water retaining agent, or sustained release agent of fertilizer or the like.

In addition, other hydrophilic monomers can also be used when forming the copolymer. Examples of the hydrophilic monomers include vinylsulfonic acid, vinylsulfonic salt, acrylsulfonic acid, acrylsulfonic salt, itaconic acid, itaconic salt, or combinations thereof. It should be noted that these hydrophilic monomers are merely examples and a scope of the disclosure is not intended to be limiting. The hydrophilic monomers in various embodiments may be any known or future developed hydrophilic monomers.

In another embodiment, a superabsorbent polymer and a method for forming the same are provided. The method for forming the superabsorbent polymer includes copolymerizing a composition including: (a) a first hydrophilic monomer, including itaconamic acid (IAm), itaconamic salt, or combinations thereof; (b) a second hydrophilic monomer, including acrylic acid (AA), acrylic salt, acrylamide (Am), or combinations thereof; and (c) a first crosslinker. In one embodiment, the composition contains 1.0 wt % to 60 wt % of the first hydrophilic monomer. In another embodiment, the composition contains 10 wt % to 50 wt % of the first hydrophilic monomer. In another embodiment, the composition contains 30 wt % to 99 wt % of acrylic acid or acrylic salt of the second hydrophilic monomer. In still another embodiment, the composition contains 45 wt % to 90 wt % of acrylic acid or acrylic salt of the second hydrophilic monomer. In addition, the composition may contain 1.0 wt % to 60 wt % of acrylamide of the second hydrophilic monomer, for example. In another embodiment, the composition contains 10 wt % to 33 wt % of acrylamide of the second hydrophilic monomer. In addition, the itaconamic salt and acrylic salt may refer to, for example, their lithium salt, sodium salt, potassium salt, magnesium salt, aluminum salt, calcium salt, or combinations thereof. Examples of the first crosslinker includes N,N'-methylenebisacrylamide, polyethylene glycol diacrylate, trimethylolpropane ethoxylate triacrylate, pentaerythritol triacrylate, or combinations thereof. The crosslinker may be present in an amount of 0.5 wt % to 3 wt % of the total amount of the first hydrophilic monomer and the second hydrophilic monomer, wherein the amount of the crosslinker refers to a weight ratio between the crosslinker and the total amount of itaconamic acid, acrylic acid, and acrylamide, for example.

In one embodiment, the composition contains more than 10 wt % of the first hydrophilic monomer. For example, the composition contains 10 wt % to 60 wt % of the first hydrophilic monomer. In another embodiment, the composition contains 10 wt % to 50 wt % of the first hydrophilic monomer. However, a second crosslinker may further be added to the resulting oligomers to perform a post-crosslinking reaction. Therefore, a superabsorbent polymer can still be formed by the post-crosslinking reaction. Examples of the second crosslinker include N,N'-methylenebisacrylamide, polyethylene glycol diacrylate, trimethylolpropane ethoxylate triacrylate, pentaerythritol triacrylate, or combinations thereof. The crosslinker may be present in an amount of 0.5 wt % to 3 wt % of the total amount of the first hydrophilic monomer and the second hydrophilic monomer, wherein the amount of the crosslinker refers to a weight ratio between the crosslinker and the total amount of itaconamic acid, acrylic acid, and acrylamide, for example. In another embodiment, the crosslinker may be present in an amount of 1 wt % of the total amount of the first hydrophilic monomer and the second hydrophilic monomer.

The superabsorbent polymer formed from itaconamic acid/salt has a better water absorption rate than poly(acrylic acid-co-acrylamide) formed from acrylic acid and acrylamide.

Figure 1:
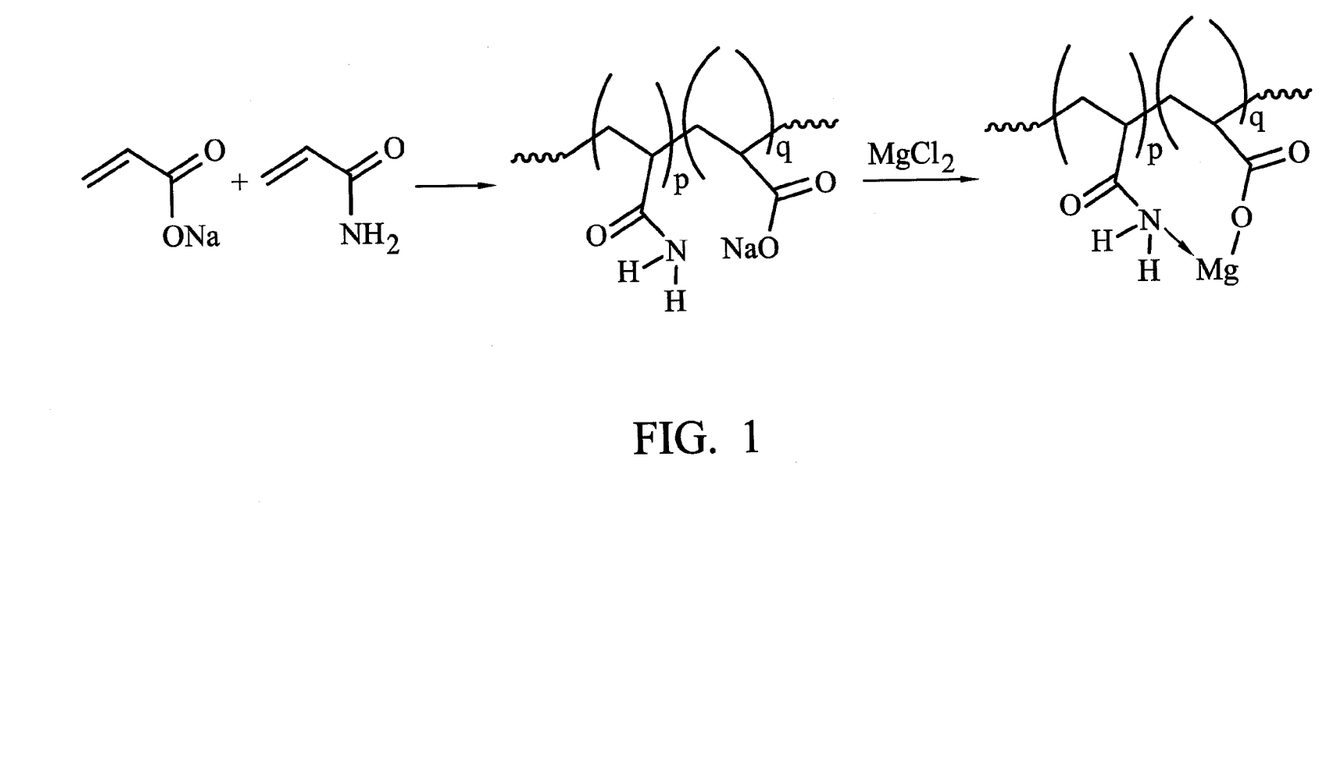
FIG. 1 illustrates a superabsorbent polymer formed from acrylic acid and acrylamide in one comparative embodiment.

FIG. 1 illustrates a superabsorbent polymer formed from acrylic acid and acrylamide, wherein p, q are respectively positive integers. The negative charge repulsion between the carboxylic group (COO$^-$) of the acrylic acid may lead to volume expansion of the superabsorbent polymer and increase of the osmotic pressure. Therefore, the superabsorbent polymer can have water absorption ability. In addition, the carboxylic group of the acrylic acid and the amino group of the acrylamine may chelate to a cation in the solution to form a stable chelated complex, and therefore the common ion effect in the solution may decrease.

The superabsorbent polymer formed from acrylic acid and acrylamide may have unsatisfactory water absorption ability due to the following reasons:

(1) An amount of the carboxylic group per unit volume may be too low, and therefore the expansion volume of the superabsorbent polymer is small. Although the common ion effect may decrease due to the presence of the acryamide, the acylamide does not have any negative charges, such that no repulsion is present between the acrylamide. Therefore, the water absorption ability is compromised. Thus, the more acrylamide used to form the polymer, the smaller the possible expansion volume and the water absorption ability becomes.

(2) A rigidity of the functional group on the main chain may be too high, and therefore it is difficult to form a chelated complex. In a superabsorbent polymer formed from acrylic acid and acrylamide, the carboxylic group and amino group are both located on the main chain bonded by a $SP^2$ carbon, and therefore the carboxylic group and amino group will have high rigidity and can not freely rotate. Since, a rotation of the carboxylic group and amino group will result in a twist of the main chain, it is difficult for a chelated complex to be formed.

(3) A distance between two functional groups may be varied, and therefore it is difficult to form a chelated complex is difficult. Although the carboxylic group and the amino group are adjacent to each other in FIG. 1, it is simply for illustration and several acrylic acids (or several acrylamines) may be bonded to each other in reality during polymerization. In other words, the carboxylic group and the amino group may not be adjacent to each other but spaced apart by a larger distance (having several monomers in between.) Therefore, it ma be difficult to form a chelated complex.

(4) A cation may be chelated to functional groups located on various main chains, resulting in a limitation of the expansion volume of the superabsorbent polymer. When the carboxylic group and the amino group on the same main chain are spaced apart from each other, the chelated complex tends to be formed by the carboxylic group and the amino group on different main chains. For example, a carboxylic group on a first main chain and an amino group on a second main chain may chelate to a same cation, resulting in a confined distance between the first main chain and the second main chain. Therefore, an expansion volume of the superabsorbent polymer and the water absorption ability are limited.

Figure 2:
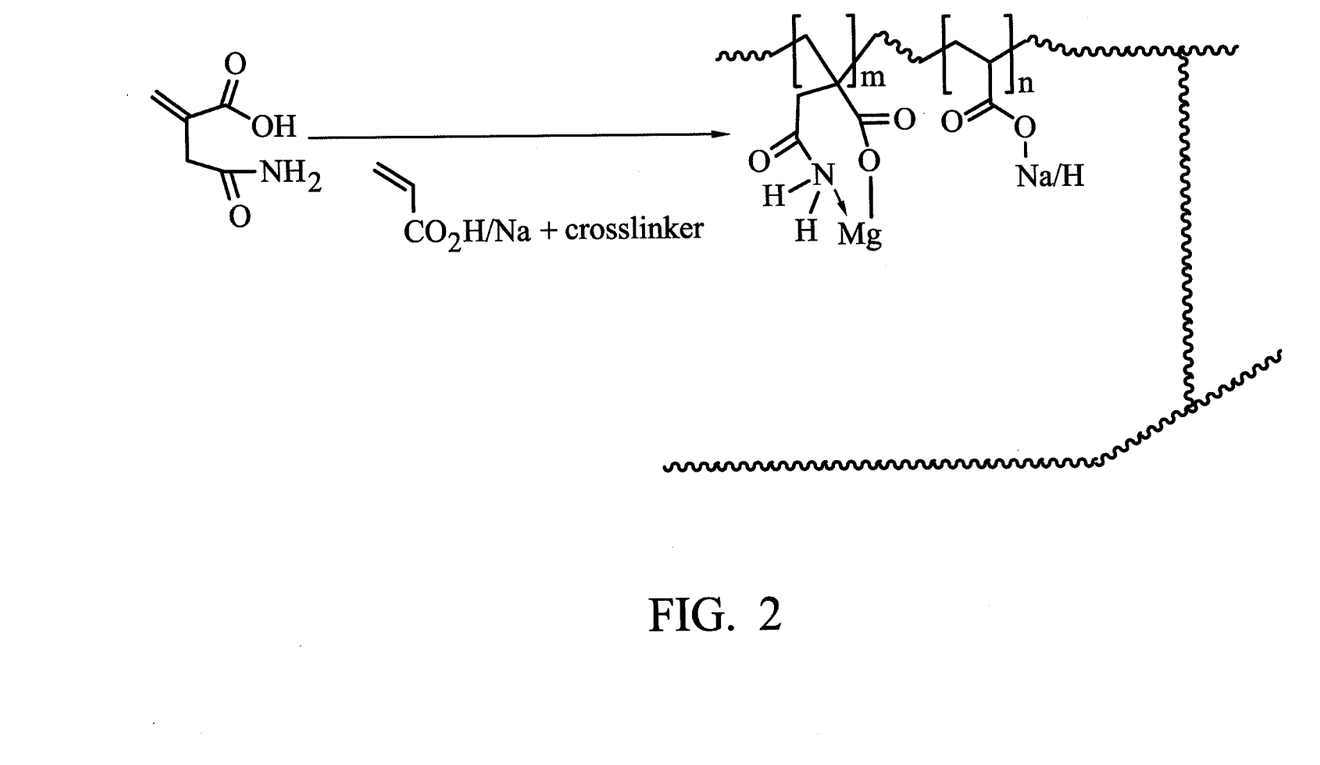
FIG. 2 is illustrates a superabsorbent polymer formed from acrylic acid and itaconamic acid in one exemplary embodiment.

FIG. 2 illustrates a superabsorbent polymer formed from acrylic acid (AA) and itaconamic acid (IAm), wherein m and n are respectively positive integers. It should be noted that the superabsorbent polymer in FIG. 2 is merely an example and a scope of the disclosure is not intended to be limiting. In some embodiments, other hydrophilic monomers may be used to form the superabsorbent polymer accompanying with the itaconamic acid and/or itaconamic salt.

As shown in FIG. 2, both the itaconamic acid and acrylic acid have carboxylic group (COO$^-$) with negative charges, and therefore repulsion between those negative charges will result in more expansion in the superabsorbent polymer structure and the water absorption ability can be improved. In addition, the carboxylic group and the amino group on one itaconamic acid (IAm) can chelate to a cation in the solution to form a stable chelated complex, and therefore the common ion effect in the solution may decrease.

The superabsorbent polymer formed from acrylic acid and itaconamic acid also has the following properties.

(1) An amount of the carboxylic group per unit volume is high, and therefore a water absorption ability of the superabsorbent polymer is improved. Since each itaconamic acid has both the carboxylic group and the amino group, the amount of the carboxylic group will not decrease due to the increased amount of the itaconamic acid. Therefore, the resulting polymer has a sufficient amino group to decrease the common ion effect, without compromising the high density of the carboxylic group per unit volume.

(2) The functional groups on the main chain can rotate freely, and therefore it is easier to form a chelated complex. In a superabsorbent polymer formed from acrylic acid and itaconamic acid, the amino group is bonded to the main chain of the network structure of the superabsorbent polymer by an $SP^3$ carbon, and therefore the amino group can rotate freely. In other words, a rotation of the amino group will not result in a twist of the main chain, and therefore, it is easier for the polymer to form a chelated complex.

(3) A distance between two functional groups is fixed, and therefore it is easier to form a chelated complex. Since both the carboxylic group and the amino group are located on the itaconamic acid and a distance between the carboxylic group and the amino group is fixed, forming a chelated complex can be fast and easy. In addition, since each itaconamic acid can form a chelated complex with a cation by itself, the possibility of a chelated complex formed by chelating to the carboxylic group and the amino group on different main chains decreases.

Accordingly, an amount of the carboxylic group in the superabsorbent polymer (formed from itaconamic acid) per unit volume is high, and therefore it can have a good water absorption ability and water retaining capacity. For example, in distilled water, a water absorption rate of a conventional absorbent polymer is usually about 105 g/g to 120 g/g. However, a water absorption rate of the superabsorbent polymer in various embodiments of the disclosure can reach about 150 g/g to 250 g/g. In addition, since each itaconamic acid has both a carboxylic group and an amino group, it is easier for the polymer to form a chelated complex with a cation in the solution, such that the water absorption ability of the resulting superabsorbent polymer in a silane solution can be better than a conventional absorbent polymer. For example, in a silane solution (0.9 wt % of sodium chloride), a water absorption rate of a conventional absorbent polymer is only about 25 g/g to 30 g/g. However, a water absorption rate of the superabsorbent polymer in various embodiment of the disclosure may reach about 35 g/g to 50 g/g.

COMPARATIVE EXAMPLE 1

Synthesis of an Absorbent Polymer: Containing Acrylic Acid Monomer (90 wt %) and Acrylamide Monomer (10 wt %)

(1) Preparation of a Reaction Solution:
10.3 g of NaOH was added into 70 g of water in an ice bath. After the NaOH was dissolved, 27 g of the acrylic acid and 3 g of acrylamide were slowly added into the solution in the ice bath. The solution was warmed to room temperature and 0.3 g of the N,N'-methylenebisacrylamide (MBAA) was added and dissolved in the solution. Next, 0.3 g of initiator 4,4'-azobis(4-cyanovaleric acid) (CAS Number: 2638-94-0) was added and dissolved in the solution, and the solution was left to stand for subsequent use.

(2) Polymerization:
The reaction solution was placed in an oil pot and stirred at 70° C. for 30 minutes to form a product. After the solution cooled down, 3000 ml of distilled water was used to wash the product for 3 times. Finally, the product was filtered and dried in an ordinary oven at 80° C. for 48 hours. Then, the product was dried in a vacuum oven at 70° C. for 48 hours to obtain the dried product.

(3) Water Absorption Ability Test:
0.5 of the resulting product was placed into a hydrophilic polypropylene (PP) non-woven sack. The sack was put into distilled water or a 0.9 wt % of an NaCl solution for 6 hours. Then, the sack was taken out of the solution and centrifuged for 3 minutes (1500 rpm.) The weight of the sack was weighed and the water absorption rate was analyzed.

In addition, the product was acidified by 0.1M of hydrochloric acid at a low temperature. The product was washed by distilled water to reach a pH value of 6 and then was dried. The resulting product was then analyzed by an $^1$H-NMR and $^{13}$C-NMR. The result showed that a ratio of the acrylic acid monomer to the acrylamide monomer in the copolymer was 90.1:9.9.

COMPARATIVE EXAMPLE 2

Synthesis of an Absorbent Polymer: Containing Acrylic Acid Monomer (80 wt %) and Acrylamide Monomer (20 wt %)

(1) Preparation of a Reaction Solution:
9.4 g of NaOH was added into 70 g of water in an ice bath. After the NaOH was dissolved, 36 g of the acrylic acid and 9 g of acrylamide were slowly added into the solution in the ice bath. The solution was warmed to room temperature and 0.45 g of the N,N'-methylenebisacrylamide (MBAA) was added and dissolved in the solution. Next, 0.45 g of initiator 4,4'-azobis(4-cyanovaleric acid) (CAS Number: 2638-94-0) was added and dissolved in the solution, and the solution was left to stand for subsequent use. The 4,4'-azobis(4-cyanovaleric acid) was present in an amount of 1 wt % of the total amount of the acrylic acid and acrylamide.

(2) Polymerization:
The reaction solution was placed in an oil pot and stirred at 70° C. for 30 minutes to form a product. After the solution cooled down, 3000 ml of distilled water was used to wash the product for 3 times. Finally, the product was filtered and dried in an ordinary oven at 80° C. for 48 hours. Then, the product was dried in a vacuum oven at 70° C. for 48 hours to obtain the dried product.

(3) Water Absorption Ability Test:
0.5 of the resulting product was placed into a hydrophilic polypropylene (PP) non-woven sack. The sack was put into distilled water or a 0.9 wt % of an NaCl solution for 6 hours. Then, the sack was taken out of the solution and centrifuged for 3 minutes (1500 rpm.) The weight of the sack was weighed and the water absorption rate was analyzed.

In addition, the product was acidified by 0.1M of hydrochloric acid at a low temperature. The product was washed by distilled water to reach a pH value of 6 and then was dried. The resulting product was then analyzed by an $^1$H-NMR and $^{13}$C-NMR. The result showed that a ratio of the acrylic acid monomer to the acrylamide monomer in the copolymer was 78.9:21.1.

COMPARATIVE EXAMPLE 3

Synthesis of an Absorbent Polymer: Containing Acrylic Acid Monomer (70 wt %) and Acrylamide Monomer (30 wt %)

(1) Preparation of a Reaction Solution:
9.4 g of NaOH was added into 70 g of water in an ice bath. After the NaOH was dissolved, 21 g of the acrylic acid and 9 g of acrylamide were slowly added into the solution in the ice bath. The solution was warmed to room temperature and 0.3 g of the N,N'-methylenebisacrylamide (MBAA) was added and dissolved in the solution. Next, 0.3 g of initiator 4,4'-azobis(4-cyanovaleric acid) (CAS Number: 2638-94-0) was added and dissolved in the solution, and the solution was left to stand for subsequent use. The 4,4'-azobis(4-cyanovaleric acid) was present in an amount of 1 wt % of the total amount of the acrylic acid and acrylamide.

(2) Polymerization:

The reaction solution was placed in an oil pot and stirred at 70° C. for 30 minutes to form a product. After the solution cooled down, 3000 ml of distilled water was used to wash the product for 3 times. Finally, the product was filtered and dried in an ordinary oven at 80° C. for 48 hours. Then, the product was dried in a vacuum oven at 70° C. for 48 hours to obtain the dried product.

(3) Water Absorption Ability Test:

0.5 of the resulting product was placed into a hydrophilic polypropylene (PP) non-woven sack. The sack was put into distilled water or a 0.9 wt % of an NaCl solution for 6 hours. Then, the sack was taken out of the solution and centrifuged for 3 minutes (1500 rpm.) The weight of the sack was weighed and the water absorption rate was analyzed.

In addition, the product was acidified by 0.1M of hydrochloric acid at a low temperature. The product was washed by distilled water to reach a pH value of 6 and then was dried. The resulting product was then analyzed by an $^1$H-NMR and $^{13}$C-NMR. The result showed that a ratio of the acrylic acid monomer to the acrylamide monomer in the copolymer was 68.3:31.7.

COMPARATIVE EXAMPLE 4

Synthesis of an Absorbent Polymer: Containing Acrylic Acid Monomer (100 wt %)

(1) Preparation of a Reaction Solution:

16.2 g of NaOH was added into 105 g of water in an ice bath. After the NaOH was dissolved, 45 g of the acrylic acid was slowly added into the solution in the ice bath. The solution was warmed to room temperature and 0.45 g of the N,N'-methylenebisacrylamide (MBAA) was added and dissolved in the solution. Next, 0.45 g of initiator 4,4'-azobis(4-cyanovaleric acid) (CAS Number: 2638-94-0) was added and dissolved in the solution, and the solution was left to stand for subsequent use. The initiator 4,4'-azobis(4-cyanovaleric acid) was present in an amount of 1 wt % of the total amount of the acrylic acid monomer.

(2) Polymerization:

The reaction solution was placed in an oil pot and stirred at 70° C. for 30 minutes to form a product. After the solution cooled down, 3000 ml of distilled water was used to wash the product for 3 times. Finally, the product was filtered and dried in an ordinary oven at 80° C. for 48 hours. Then, the product was dried in a vacuum oven at 70° C. for 48 hours to obtain the dried product.

(3) Water Absorption Ability Test:

0.5 of the resulting product was placed into a hydrophilic polypropylene (PP) non-woven sack. The sack was put into distilled water or a 0.9 wt % of an NaCl solution for 6 hours. Then, the sack was taken out of the solution and centrifuged for 3 minutes (1500 rpm.) The weight of the sack was weighed and the water absorption rate was analyzed.

EXAMPLE 1

Synthesis of Itaconamic Acid (1) Synthesis 8.6 ml of ammonia (28 wt %) was placed into a flask (50 ml) at room temperature, and 5 g of itaconic anhydride was separately added into the flask, three times. The mixture was stirred for 3 hors at room temperature, and then 25 ml of sulfuric acid (4M) was also added into the flask. The mixture was stirred continuously for 18 hours at room temperature. Next, the mixture was filtered to obtain a solid product. The product was washed by 10 ml of hydrochloric acid (0.1M) to obtain a crude product. Finally, 5 ml of ethanol was added to the crude product and stirred for 4 hours at room temperature. Then, the product was filtered and washed again by 10 ml of ethanol to obtain a purified product.

(2) Analysis

The resulting product was dissolved in $d^6$-DSMO for analysis by an NMR. The results of the $^1$H-NMR and $^{13}$C-NMR showed the following peaks: $^1$H-NMR (400 MHz, $d^6$-DMSO) δ ppm=12.44 (1H, OH, br, s), 7.28 (1H, NH, s), 6.81 (1H, NH, s), 6.08 (1H, CCH$_2$, s), 5.63, CCH$_2$, s), 0.05 (2H, CH$_2$, s). $^{13}$C-NMR (400 MHz, $d^6$-DMSO) δ ppm=172.0 (1C, C(O)), 168.2 (1C, C(O)), 136.7, 127.4, 38.8.

EXAMPLE 2

Synthesis of a Copolymer: Acrylic Acid (40 wt %)-Acrylamide (40 wt %)-Itaconamic Acid (20 wt %)

(1) Preparation of a Reaction Solution:

20 g of acrylic acid, 20 g of acrylamide, 10 g of itaconamic acid, 0.45 of initiator 4,4'-azobis(4-cyanovaleric acid), and 117 g of water were mixed to obtain the reaction solution. The 4,4'-azobis(4-cyanovaleric acid) was present in an amount of 1 wt % of the total amount of the acrylic acid, acrylamide, and itaconamic acid.

(2) Polymerization:

The reaction solution was placed in an oil pot and stirred at 70° C. for 30 minutes to form a product. After the solution cooled down, 3000 ml of distilled water was used to wash the product for 3 times. Finally, the product was filtered and dried in an ordinary oven at 80° C. for 48 hours. Then, the product was dried in a vacuum oven at 70° C. for 48 hours to obtain the dried product. The yield of the copolymer was 91%. The viscosity (BrookField) was 7.8 cP. The weight-average molecular weight was 20,000 g/mole. The degree of neutralization was 65%.

In addition, the results of the $^1$H-NMR and $^{13}$C-NMR showed the following peaks: $^{13}$C-NMR (400 MHz, d6-DMSO) δ ppm=179-170. (1C, C(O)), 167-164 (1C, C(O)). A ratio of the acrylic acid monomer to the acrylamide monomer to the itaconamic acid monomer in the copolymer was 38.1:42.7:19.2.

EXAMPLE 3

Synthesis of a Copolymer: Acrylic Acid (90 wt %)-Itaconamic Acid (10 wt %)

The same procedure as in Example 2 was repeated in Example 3 except that the hydrophilic monomers were 45 g of acrylic acid and 5 g of itaconamic acid. The initiator 4,4'-azobis(4-cyanovaleric acid) was present in an amount of 1 wt % of the total amount of the acrylic acid and itaconamic acid. The yield of the copolymer was 88%. The viscosity (BrookField) was 7.9 cP. The weight-average molecular weight was 23,000 g/mole.

In addition, the results of the $^1$H-NMR and $^{13}$C-NMR showed the following peaks: $^{13}$C-NMR (400 MHz, d6-DMSO) δ ppm=178-170. (1C, C(O)), 167-166 (1C, C(O)). A ratio of the acrylic acid monomer to the itaconamic acid monomer in the copolymer was 87.7:12.3.

EXAMPLE 4

Synthesis of a Copolymer: Acrylic Acid (70 wt %)-Itaconamic Acid (30 wt %)

The same procedure as in Example 2 was repeated in Example 4 except that the hydrophilic monomers were 35 g of acrylic acid and 15 g of itaconamic acid. The initiator 4,4'-azobis(4-cyanovaleric acid) was present in an amount of 1 wt % of the total amount of the acrylic acid and itaconamic acid. The yield of the copolymer was 61%. The viscosity (Brook-Field) was 3.0 cP. The weight-average molecular weight was 11,000 g/mole.

In addition, the results of the $^1$H-NMR and $^{13}$C-NMR showed the following peaks: $^{13}$C-NMR (400 MHz, d6-DMSO) δ ppm=178-170. (1C, C(O)), 167-164 (1C, C(O)). A ratio of the acrylic acid monomer to the itaconamic acid monomer in the copolymer was 75.2:24.8.

EXAMPLE 5

Synthesis of a Superabsorbent Polymer: Containing Acrylic Acid Monomer (90 wt %) and Itaconamic Acid Monomer (10 wt %)

(1) Preparation of a Reaction Solution:

10.3 g of NaOH was added into 70 g of water in an ice bath. After the NaOH was dissolved, 27 g of the acrylic acid and 3 g of itaconamic acid were slowly added into the solution in the ice bath. The solution was warmed to room temperature and 0.3 g of the N,N'-methylenebisacrylamide (MBAA) was added and dissolved in the solution. Next, 0.3 g of initiator 4,4'-azobis(4-cyanovaleric acid) (CAS Number: 2638-94-0) was added and dissolved in the solution, and the solution was left to stand for subsequent use. The initiator 4,4'-azobis(4-cyanovaleric acid) was present in an amount of 1 wt % of the total amount of the acrylic acid and itaconamic acid.

(2) Polymerization:

The reaction solution was placed in an oil pot and stirred at 70° C. for 30 minutes to form a product. After the solution cooled down, 3000 ml of distilled water was used to wash the product for 3 times. Finally, the product was filtered and dried in an ordinary oven at 80° C. for 48 hours. Then, the product was dried in a vacuum oven at 70° C. for 48 hours to obtain the dried product. The yield of the dried product was 96%. The viscosity (BrookField) was 3-4 cP. The weight-average molecular weight was 10,000 g/mole.

(3) Water Absorption Ability Test:

0.5 of the resulting product was placed into a hydrophilic polypropylene (PP) non-woven sack. The sack was put into distilled water or a 0.9 wt % of an NaCl solution for 6 hours. Then, the sack was taken out of the solution and centrifuged for 3 minutes (1500 rpm.) The weight of the sack was weighed and the water absorption rate was analyzed.

In addition, the product was acidified by 0.1M of hydrochloric acid at a low temperature. The product was washed by distilled water to reach a pH value of 6 and then was dried. The resulting product was then analyzed by an $^1$H-NMR and $^{13}$C-NMR. The result showed $^{13}$C-NMR (400 MHz, d6-DMSO) δ ppm=174-170. (1C, C(O)), 168-165 (1C, C(O)). A ratio of the acrylic acid monomer to the itaconamic acid monomer was 89.0:11.0. A ratio of carbon to hydrogen to oxygen to nitrogen was 47.66%:6.12%:45.09%:1.13% (theoretical ratio was 49.65%:5.54%:43.72%:1.09%).

EXAMPLE 6

Synthesis of a Superabsorbent Polymer: Containing Acrylic Acid Monomer (80 wt %) and Itaconamic Acid Monomer (20 wt %)

(1) Preparation of a Reaction Solution:

14.8 g of NaOH was added into 105 g of water in an ice bath. After the NaOH was dissolved, 36 g of the acrylic acid and 9 g of itaconamic acid were slowly added into the solution in the ice bath. The solution was warmed to room temperature and 0.45 g of the N,N'-methylenebisacrylamide (MBAA) was added and dissolved in the solution. Next, 0.45 g of initiator 4,4'-azobis(4-cyanovaleric acid) (CAS Number: 2638-94-0) was added and dissolved in the solution, and the solution was left to stand for subsequent use. The 4,4'-azobis(4-cyanovaleric acid) was present in an amount of 1 wt % of the total amount of the acrylic acid and itaconamic acid.

(2) Polymerization:

The reaction solution was placed in an oil pot and stirred at 70° C. for 30 minutes to form a product. After the solution cooled down, 3000 ml of distilled water was used to wash the product for 3 times. Finally, the product was filtered and dried in an ordinary oven at 80° C. for 48 hours. Then, the product was dried in a vacuum oven at 70° C. for 48 hours to obtain the dried product. The yield of the dried product was 89%.

(3) Water Absorption Ability Test:

0.5 of the resulting product was placed into a hydrophilic polypropylene (PP) non-woven sack. The sack was put into distilled water or a 0.9 wt % of an NaCl solution for 6 hours. Then, the sack was taken out of the solution and centrifuged for 3 minutes (1500 rpm.) The weight of the sack was weighed and the water absorption rate was analyzed.

In addition, the product was acidified by 0.1M of hydrochloric acid at a low temperature. The product was washed by distilled water to reach a pH value of 6 and then was dried. The resulting product was then analyzed by an $^1$H-NMR and $^{13}$C-NMR. The result showed $^{13}$C-NMR (400 MHz, d6-DMSO) δ ppm=174-170. (1C, C(O)). A ratio of the acrylic acid monomer to the itaconamic acid monomer was 79.2:20.8. A ratio of carbon to hydrogen to oxygen to nitrogen was 50.77%:5.94%:41.20%:2.09% (theoretical ratio was 49.30%:5.53%:42.99%:2.18%).

EXAMPLE 7

Synthesis of a Superabsorbent Polymer: Containing Acrylic Acid Monomer (70 wt %) and Itaconamic Acid Monomer (30 wt %)

(1) Preparation of a Reaction Solution:

9.4 g of NaOH was added into 70 g of water in an ice bath. After the NaOH was dissolved, 21 g of the acrylic acid and 9 g of itaconamic acid were slowly added into the solution in the ice bath. The solution was warmed to room temperature and 0.3 g of the N,N'-methylenebisacrylamide (MBAA) was added and dissolved in the solution. Next, 0.3 g of initiator 4,4'-azobis(4-cyanovaleric acid) (CAS Number: 2638-94-0) was added and dissolved in the solution, and the solution was left to stand for subsequent use. The 4,4'-azobis(4-cyanovaleric acid) was present in an amount of 1 wt % of the total amount of the acrylic acid and itaconamic acid.

(2) Polymerization:

The reaction solution was placed in an oil pot and stirred at 70° C. for 30 minutes to form a product. After the solution cooled down, 3000 ml of distilled water was used to wash the product for 3 times. Finally, the product was filtered and dried in an ordinary oven at 80° C. for 48 hours. Then, the product was dried in a vacuum oven at 70° C. for 48 hours to obtain the dried product. The yield of the dried product was 85%.

(3) Water Absorption Ability Test:

0.5 of the resulting product was placed into a hydrophilic polypropylene (PP) non-woven sack. The sack was put into distilled water or a 0.9 wt % of an NaCl solution for 6 hours. Then, the sack was taken out of the solution and centrifuged for 3 minutes (1500 rpm.) The weight of the sack was weighed and the water absorption rate was analyzed. In addition, the product was acidified by 0.1M of hydrochloric acid at a low temperature. The product was washed by distilled water to reach a pH value of 6 and then was dried. The resulting product was then analyzed by an $^1$H-NMR and $^{13}$C-NMR. The result showed $^{13}$C-NMR (400 MHz, d6-DMSO) δ ppm=174-170. (1C, C(O)), 168-165 (1C, C(O)). A ratio of the acrylic acid monomer to the itaconamic acid monomer was 71.4:28.6. A ratio of carbon to hydrogen to oxygen to nitrogen was 47.27%:6.87%:42.47%:3.39% (theoretical ratio was 48.95%:5.52%:42.27%:3.26%).

EXAMPLE 8

Synthesis of a Superabsorbent Polymer: Containing Acrylic Acid Monomer (50 wt %) and Itaconamic Acid Monomer (50 wt %)

(1) Preparation of a Reaction Solution:

9.4 g of NaOH was added into 70 g of water in an ice bath. After the NaOH was dissolved, 15 g of the acrylic acid and 15 g of itaconamic acid were slowly added into the solution in the ice bath. The solution was warmed to room temperature and 0.3 g of the N,N'-methylenebisacrylamide (MBAA) was added and dissolved in the solution. Next, 0.3 g of initiator 4,4'-azobis(4-cyanovaleric acid) (CAS Number: 2638-94-0) was added and dissolved in the solution, and the solution was left to stand for subsequent use. The 4,4'-azobis(4-cyanovaleric acid) was present in an amount of 1 wt % of the total amount of the acrylic acid and itaconamic acid.

(2) Polymerization:

The reaction solution was placed in an oil pot and stirred at 70° C. for 30 minutes to form a product. After the solution cooled down, 3000 ml of distilled water was used to wash the product for 3 times. Finally, the product was filtered and dried in an ordinary oven at 80° C. for 48 hours. Then, the product was dried in a vacuum oven at 70° C. for 48 hours to obtain the dried product. The yield of the dried product was 21%.

(3) Water Absorption Ability Test:

0.5 of the resulting product was placed into a hydrophilic polypropylene (PP) non-woven sack. The sack was put into distilled water or a 0.9 wt % of an NaCl solution for 6 hours. Then, the sack was taken out of the solution and centrifuged for 3 minutes (1500 rpm.) The weight of the sack was weighed and the water absorption rate was analyzed. In addition, the product was acidified by 0.1M of hydrochloric acid at a low temperature. The product was washed by distilled water to reach a pH value of 6 and then was dried. The resulting product was then analyzed by an $^1$H-NMR and $^{13}$C-NMR. The result showed $^{13}$C-NMR (400 MHz, d6-DMSO) δ ppm=174-170. (1C, C(O)), 168-165 (1C, C(O)). A ratio of the acrylic acid monomer to the itaconamic acid monomer was 46.3:53.7.

EXAMPLE 9

Synthesis of a Superabsorbent Polymer: Containing Acrylic Acid Monomer (30 wt %) and Itaconamic Acid Monomer (70 wt %)

(1) Preparation of a Reaction Solution:

9.4 g of NaOH was added into 70 g of water in an ice bath. After the NaOH was dissolved, 9 g of the acrylic acid and 21 g of itaconamic acid were slowly added into the solution in the ice bath. The solution was warmed to room temperature and 0.3 g of the N,N'-methylenebisacrylamide (MBAA) was added and dissolved in the solution. Next, 0.3 g of initiator 4,4'-azobis(4-cyanovaleric acid) (CAS Number: 2638-94-0) was added and dissolved in the solution, and the solution was left to stand for subsequent use. The 4,4'-azobis(4-cyanovaleric acid) was present in an amount of 1 wt % of the total amount of the acrylic acid and itaconamic acid.

(2) Polymerization—Step A:

The reaction solution was placed in an oil pot and stirred at 70° C. for 30 minutes to form a product. The yield of the dried product was less than 5%.

(3) Polymerization—Step B (an Additional Crosslinker was Added after the First Step):

0.3 g of trimethylolpropane ethoxylate triacrylate was added into the reaction solution of step A as a crosslinker. Then, the procedure in step A was repeated to obtain more precipitate. The yield of the dried product was 17%. The resulting product was then analyzed by an $^1$H-NMR and $^{13}$C-NMR and a ratio of the acrylic acid monomer to the itaconamic acid monomer was 40.8:59.2.

EXAMPLE 10

Synthesis of a Superabsorbent Polymer: Containing Itaconamic Acid Monomer (100 wt %)

(1) Preparation of a Reaction Solution:

9.4 g of NaOH was added into 70 g of water in an ice bath. After the NaOH was dissolved, 30 g of itaconamic acid was slowly added into the solution in the ice bath. The solution was warmed to room temperature and 0.3 g of the N,N'-methylenebisacrylamide (MBAA) was added and dissolved in the solution. Next, 0.3 g of initiator 4,4'-azobis(4-cyanovaleric acid) (CAS Number: 2638-94-0) was added and dissolved in the solution, and the solution was left to stand for subsequent use. The 4,4'-azobis(4-cyanovaleric acid) was present in an amount of 1 wt % of the amount of the itaconamic acid.

(2) Polymerization—Step A:

The reaction solution was placed in an oil pot and stirred at 70° C. for 30 minutes to form a product. The yield of the dried product was less than 5%.

(3) Polymerization—Step B (an Additional Crosslinker was Added after the First Step):

0.3 g of trimethylolpropane ethoxylate triacrylate was added into the reaction solution of step A as a crosslinker. Then, the procedure in step A was repeated to obtain more precipitate. The yield of the dried product was 14%.

EXAMPLE 11

Water Absorption Ability

Table 1 (as shown below) illustrates the water absorption rates of the superabsorbent polymers in Examples 5 to 8 and Comparative examples 1 to 4. As shown in Table 1, in distilled water, the water absorption rates of the superabsorbent polymers containing itocanamic acid (IAm) monomer (Examples 5 to 8) was much higher than the water absorption rates of the superabsorbent polymers containing only acrylic acid (AA) monomer and acrylamine (AM) monomer (Comparative Examples 1 to 4), resulting from a higher density of the carboxylic group and the amino group in the itocanamic monomer. In addition, in a solution containing salt, the water absorption rates of the superabsorbent polymers containing the itocanamic acid (IAm) monomer (Examples 5 to 8) was also higher than the water absorption rates of the superabsorbent polymers containing only the acrylic acid (AA) monomer and acrylamine (AM) monomer (Comparative Examples 1 to 4). A possible reason is that each itaconamic acid had both the carboxylic group and amino group, and therefore a chelated complex formed by the carboxylic group, amino group, and a cation could be formed easier.

TABLE 1

| | AA (wt %) | IAm (wt %) | AM (wt %) | Water absorption ability in DI water (g/g) | Water absorption ability in silane (g/g), |
|---|---|---|---|---|---|
| Example 5 | 89.0 | 11.0 | 0 | 157 | 37 |
| Example 6 | 79.2 | 20.8 | 0 | 155 | 38 |
| Example 7 | 71.4 | 28.6 | 0 | 233 | 48 |
| Example 8 | 46.3 | 53.7 | 0 | 216 | 51 |
| Comparative Example 1 | 90.1 | 0 | 9.9 | 110 | 30 |
| Comparative Example 2 | 78.9 | 0 | 21.1 | 116 | 29 |
| Comparative Example 3 | 68.3 | 0 | 31.7 | 108 | 30 |
| Comparative Example 4 | 100 | 0 | 0 | 117 | 28 |

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A copolymer copolymerized from a composition comprising:
   (a) a first hydrophilic monomer, comprising itocanamic acid, itocanamic salt, or combinations thereof; and
   (b) a second hydrophilic monomer, comprising acrylic acid, acrylic salt, acrylamide, or combinations thereof, wherein a weight-average molecular weight of the copolymer is between 11,000 g/mole and 23,000 g/mole.

2. The copolymer as claimed in claim 1, wherein the composition further comprises (c) a third hydrophilic monomer, comprising vinylsulfonic acid, vinylsulfonic salt, acrylsulfonic acid, acrylsulfonic salt, itaconic acid, itaconic salt, or combinations thereof.

3. The copolymer as claimed in claim 1, wherein the itaconamic salt and acrylic salt respectively comprises their lithium salt, sodium salt, potassium salt, magnesium salt, aluminum salt, calcium salt, or combinations thereof.

4. The copolymer as claimed in claim 1, wherein the copolymer is used as a chelating agent, water-absorbing agent, sealant, or fire retardant.

5. The copolymer as claimed in claim 1, wherein the composition contains more than 10 wt % of the first hydrophilic monomer.

6. The copolymer as claimed in claim 1, wherein the composition contains 10 wt % to 30 wt % of the first hydrophilic monomer.

7. The copolymer as claimed in claim 1, wherein the composition contains 45 wt % to 90 wt % of the second hydrophilic monomer which is acrylic acid or acrylic salt.

8. The copolymer as claimed in claim 1, wherein the composition contains 10 wt % to 33 wt % of acrylamide of the second hydrophilic monomer which is acrylamide.

9. The copolymer as claimed in claim 1, the composition further comprises (d) a crosslinker to form a superabsorbent polymer.

10. The copolymer as claimed in claim 9, wherein the crosslinker is present in an amount of 0.5 wt % to 3 wt % of the total amount of the first hydrophilic monomer and the second hydrophilic monomer.

11. The copolymer as claimed in claim 9, wherein the crosslinker comprises N,N'-methylenebisacrylamide, polyethylene glycol diacrylate, trimethylolpropane ethoxylate triacrylate, pentaerythritol triacrylate, or combinations thereof.

12. The copolymer as claimed in claim 9, wherein the composition contains more than 10 wt % of the first hydrophilic monomer.

13. The copolymer as claimed in claim 9, wherein the composition contains 10 wt % to 50 wt % of the first hydrophilic monomer.

14. The copolymer as claimed in claim 9, wherein the composition contains 45 wt % to 90 wt % of the second hydrophilic monomer which is acrylic acid or acrylic salt.

15. The copolymer as claimed in claim 9, wherein the composition contains 10 wt % to 33 wt % of the second hydrophilic monomer which is acrylamide.

16. A method for manufacturing a copolymer, comprising copolymerizing a composition using a free radical polymerizing reaction, wherein the composition comprises:
   (a) a first hydrophilic monomer, comprising itaconamic acid, itaconamic salt, or combinations thereof; and
   (b) a second hydrophilic monomer, comprising acrylic acid, acrylic salt, acrylamide, or combinations thereof, wherein a weight-average molecular weight of the copolymer is between 11,000 g/mole and 23,000 g/mole.

17. The method for manufacturing a copolymer as claimed in claim 16, wherein the polymerizing reaction is performed in the presence of an initiator.

18. The method for manufacturing a copolymer as claimed in claim 17, wherein the initiator is present in an amount of 1.0 wt % of the total amount of the first hydrophilic monomer and the second hydrophilic monomer.

19. The method for manufacturing a copolymer as claimed in claim 17, wherein the initiator comprises 4,4'-azobis(4-cyanovaleric acid).

20. The method for manufacturing a copolymer as claimed in claim 16, wherein the composition further comprises (c) a third hydrophilic monomer, comprising vinylsulfonic acid, vinylsulfonic salt, acrylsulfonic acid, acrylsulfonic salt, itaconic acid, itaconic salt, or combinations thereof 21. The method for manufacturing a copolymer as claimed in claim 16, wherein the composition further comprises (d) a first crosslinker to form a superabsorbent polymer.

22. The method for manufacturing a copolymer as claimed in claim 21, wherein the composition contains more than 10 wt % of the first hydrophilic monomer.

23. The method for manufacturing a copolymer as claimed in claim 21, wherein the composition contains 10 wt % to 30 wt % of the first hydrophilic monomer.

24. The method for manufacturing a copolymer as claimed in claim 21, after the free radical polymerizing reaction, further comprising using (e) a second crosslinker to perform a post-crosslinking reaction.

25. The method for manufacturing a copolymer as claimed in claim 24, wherein the first crosslinker and the second crosslinker respectively comprise N,N'-methylenebisacrylamide, polyethylene glycol diacrylate, trimethylolpropane ethoxylate triacrylate, pentaerythritol triacrylate, or combinations thereof.

* * * * *